United States Patent [19]

Vax

[11] Patent Number: 5,539,481
[45] Date of Patent: Jul. 23, 1996

[54] ACUITY THERAPY APPARATUS AND METHOD THEREOF

[76] Inventor: Guennadi Vax, 109 Broad St., Apt. 102, Lynn, Mass. 01902

[21] Appl. No.: 361,682

[22] Filed: Dec. 22, 1994

[51] Int. Cl.$^6$ ........................................................ A61B 3/00
[52] U.S. Cl. ................................................ 351/203; 351/246
[58] Field of Search ..................................... 351/200, 203, 351/222, 223, 246

[56] References Cited

U.S. PATENT DOCUMENTS 4,726,672 2/1988 O'Brien et al. ........................ 351/203

FOREIGN PATENT DOCUMENTS

WO80/00405 3/1980 WIPO .................................... 351/203

Primary Examiner—William L. Sikes
Assistant Examiner—Huy Mai

[57] ABSTRACT

An exercise device for prophylaxis and improving eye acuity conditions that can be used at home or at work without any medical supervision. The device includes several visual targets, a control unit and a keyboard. The device causing one target at a time in a random order to display one of a number of predetermined characters randomly chosen. A person who use the device put equally spaced targets in front of himself or herself at a distance from 0.5' to 20' and adjust the characters displayed to minimal discernable size. During every therapy session the person must denote each character on each target through the keyboard. If the person's response is correct the next character will appear. The amount of correct responses in a session and time intervals between sessions are predetermined depending on the person's age, type of his or her activities and eye acuity conditions.

8 Claims, 2 Drawing Sheets

ACUITY THERAPY APPARATUS AND METHOD THEREOF

FIELD OF INVENTION

The invention herein presented relates to prophylaxis and treatment of eye acuity conditions where the origin of a loss of acuity or of a probability of that loss is in the retina or brain and not of a refractive/transparent nature. More specifically, the therapy applies to those who spent long periods of time for reading, watching TV, looking at a computer screen, and similar activities where the distance from eyes to observing object is not changing with time or changing very little.

BACKGROUND OF THE INVENTION

The human eye can bring objects into focus because of its lens ability to accommodate. The lens is built of layers of sells. Neatly arranged, the layers allow light to pass through without scattering. Seventy fingerlike ligaments collectively known as the ciliary zonule holds the lens in place. The fibrous ligaments, in turn, are attached to the choroid coat by the circular ciliary muscle. When the zonule pulls the perimeter of the lens, the lens stretches into a flattened shape. This posture, the resting position of the eye, requires no adjustment to bring objects more than twenty feet away into focus. For the eye to focus an object within twenty feet, the ciliary muscle contracts, relaxing the zonule's pull and allowing the lens to bulge. The nearer an object, the more the lens assumes its rounded, balloon shape. But within six or seven inches, an object reaches the "near point", beyond which the lens cannot accommodate enough to focus.

In order to support the accommodation ability of an eye within the range of 0.5–20 feet, the ciliary muscle should preserve its ability of contraction. And ciliary muscle deteriorates when not in use as well as any other muscle group in the human body. In other words, the ciliary muscle needs permanent training. Being regularly focused within the same distance from an object during a long time periods (when reading, watching TV, looking at the computer screen, and alike), the eye looses its ability to properly accommodate meaning a deterioration of ciliary muscle and a loss of acuity. Because changing of contemporary activities is unrealistic, the acuity therapy is needed. It is needed when a loss of acuity already takes place to prevent further deterioration and, depending on person's age, to fully or partly restore the acuity. It is also needed as a prophylaxis to prevent forming a hardened core (when shape of the eye lens does not change often enough) of mentioned above layers of cells that decrease accommodation. It is also needed to improve additional visual abilities, such as fixation on objects, maintaining attention for periods of time, judging relative distances of objects accurately, reading rapidly.

Methods and apparatus for increasing visual acuity are known. For example, Balliet (U.S. Pat. No. 4,408,846, Cl. 351/203) teaches a unit wherein a target is selectively moved toward or away from a person to different positions at accurately determined distances therefrom. At each of the positions, the person is required to identify the appearance of the target which is randomly changed to any one of a plurality of different appearances. The concept includes the moving of the target further away from the person whenever the identification of the target appearance is correct at a given position and moving the target closer to the person whenever the identification is incorrect. The system is adapted for increasing the far-point acuity of a myopic person, as well as increasing the visual acuity of an ametropic person. The system implies use of an optical bench wherein the target is carried, having means for incremental moving the support of the target toward or away from the person.

As one can see from the above description of the known system, it affects the visual acuity in the short range of distances about the far-point and the near-point. The system does not design for training the visual acuity in the whole range of 0.5–20' where shape of the eye lens is changing. The system also needs performing measurements and adjustments using the optical bench type equipment.

Systems where the target can be located at any distance from the person are also known. For example, O'Brien and Diamond (U.S. Pat. No. 4,726,672, Cl. 351/203) teach an exercise devise for improving poor visual acuity in which a person must identify randomly chosen figures of minimal visual stimulus. The system includes a solitary visual target, a means for randomly selecting and generating a number of various figures to be displayed on said visual target, a keyboard through which the person can respond to the figures seen on the visual target, and a means for informing the person of the correctness or incorrectness of said response. In the system means are provided for adjusting the apparent size of the displayed figure to maintain the figure displayed at a level of minimal discernable size.

The use of the system includes causing the target to randomly display at least one of a number of predetermined characters, providing the person with keyboard means to denote any of said characters, and comparing the character denote through the keyboard with the displayed character to detect and signify whether they coincide with each other. Then the apparent size of the displayed character is adjusted to maintain it at a level of minimal discernable size.

As it is indicated in the patent, it particular concern is the eye condition of amblyopia employing a hypothesis of minimal optical stimulation. The system to be operated in a darkened room or chamber. A pair of headphone speakers should be used to provide aid in the isolation of the person. The main intention is to provide an alternative to the use of so-called "patch therapy" which involves covering the non-affected eye of the person and forcing the person to function using only the affected eye.

One can see that the teaching is concerned mainly by the condition of amblyopia. The singular target can be located anywhere including the range of 0.5'–20', but in only one place at a time. Because of this condition the training of visual acuity can not be provided (and does not intend to) simultaneously in the whole range.

It is desirable for the acuity therapy apparatus and method to provide eye lens muscles training under the conditions so close to the natural eye environment as possible. In other words it is desirable to train eyes within the whole range of the lens contraction, where the targets are located as close to the person as 0.5' and as far as 20', and in between at a time. It is also desirable that the person could focus his or her eyes on targets located on different distances and appeared in a random order, exactly alike the natural conditions. It is further desirable for enhancing ciliary muscle training to stimulate the person to be concentrated on a target until the target information is correctly read, and only after that to go to another target. It is also desirable for the person to read the target characters at a level of minimal discernable size. It is desirable for the apparatus and method to provide general acuity therapy including conditions before any eye deterioration takes place. It is also desirable to provide the therapeutic value in a simple, inexpensive and fully portable apparatus that could be easily used by anyone and when in use does not require any special conditions such as darkened room or chamber, measurements, eye patch, and so forth.

SUMMARY OF THE INVENTION

The invention herein presented is an acuity therapy apparatus to improve the non-refractive acuity of a person's eyes comprising of several visual targets, a control unit, and a keyboard, wherein each of said visual targets having means to display characters, said control unit having means for randomly selecting one of said visual targets at a time and randomly generating in said visual target a character to be displayed, said keyboard having means for the person to respond to the character displayed on any of said visual target, said control unit having means for comparing said displayed character with responses from said keyboard and for further commutation in said apparatus depending on the response.

Said control unit also having means for counting right answers and turning off said apparatus when predetermined amount of right answers is achieved. Said apparatus further having a timer for signalling the start of every consecutive session.

A method for use said apparatus comprising of a step of placing before the person's eyes several visual targets located first at about 0.5' from the person, last at about 20', and some in between at about equal intervals from each other (the best results give five targets); a step of causing one target at a time in random order to display one of a number of predetermined characters randomly chosen; a step of the person to denote any of said characters the person believes he or she discerns upon said visual target; a step of comparing the character denoted through said keyboard with the displayed character; and a step of adjusting the apparent size of said displayed character upon each of said visual targets to maintain the characters displayed at a level of minimal discernable size.

Time intervals between sessions and amount of characters that should be rightly denoted during every session depend on person's age, type of his or her activities, and rate of eye condition deterioration (if any). All this may be recommended by a doctor and adjusted as an experience is accumulated.

Compared to known apparatus and methods, the present invention provides general acuity therapy that does not need any special knowledge, conditions, or measurements, and can be used with ease by anyone at home or work.

DRAWINGS

DETAILED DESCRIPTION OF THE PREFERRED EMBODIMENT

Figure 1:
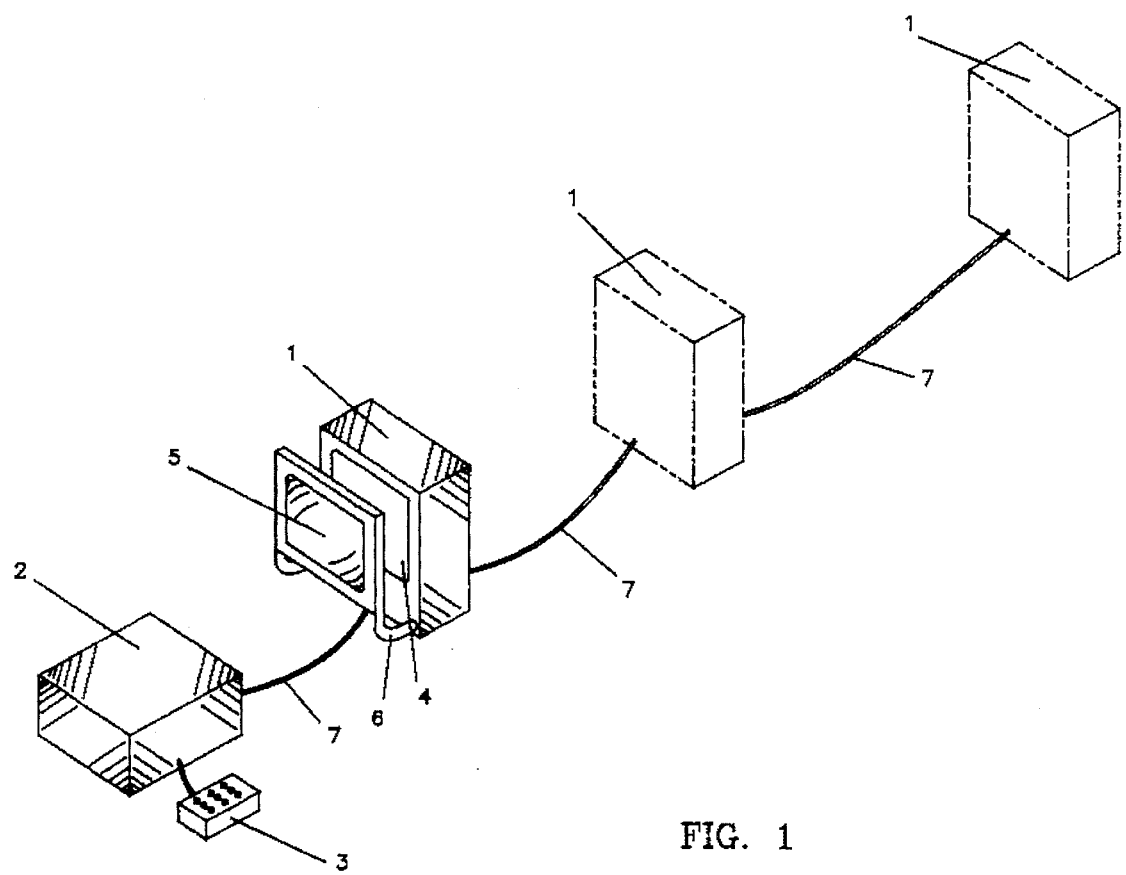
FIG. 1 is a schematic view and arrangement of the apparatus when in use according to the present invention.

Referring to the drawings FIG. 1 shows several visual targets 1, a control unit 2, and a keyboard 3 all arranged like in use. Every visual target 1 has a screen where different characters, for example numbers, can be generated by an electronic circuit located in the control unit 2. The characters may be shown on the screen of the visual target 1 by means, for example, a seven segment L.E.D. display 4. The apparent size of the displayed characters can be adjusted separately on each visual target 1 by lens 5 (not shown on all targets for clarity) by moving it on slides 6 closer or farther from the display 4. All targets 1 are connected with the control unit 2 and keyboard 3 by a cable 7 that allow to operatively locate first of the visual targets 1 at a distance of about 0.5' from the keyboard 3 (and also from a person who use the apparatus), last of the targets 1 at about 20' from the keyboard 3, and the rest of the targets 1 equally space in between the first and the last targets 1. The cable 7 segments when unfolded to the straight line provides right location for all targets 1 and no measurement is needed.

Figures 2, 3:
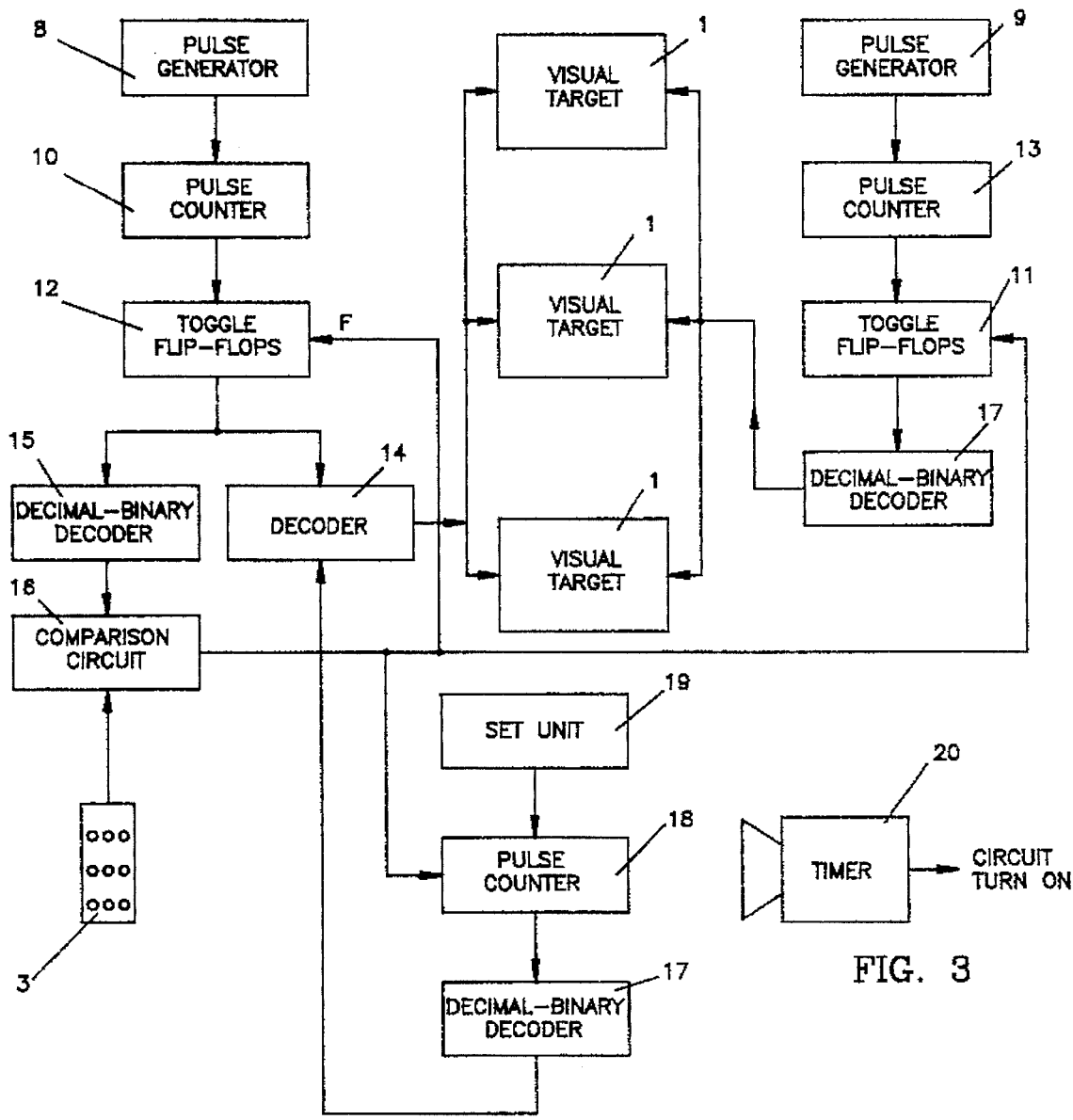
FIG. 2 is a block diagram of the electronic components according to the present invention.
FIG. 3 is a block diagram of a timer according to the present invention.

On FIG. 2 a block diagram of the electronic components of the apparatus is shown. This block diagram explains the apparatus functioning as follows. Pulse generators 8 and 9 continuously form square pulses with a frequency of about 30 KHz that are counted by pulse counters 10 and 13. Outputs of both counter 10 and counter 13 are connected with inputs of toggle flip-flops 11 and 12. Both flip-flops 11, 12 produce output signals in a binary code when pulse is coming to their complementing input "F". A train of pulses "0, 1" from the output of the flip-flop 12 go to a decoder 14 and further to all the seven segment L.E.D. displays 4 of targets 1. But only one of the L.E.D. will glow, the one that will receive a pulse from decimal-binary decoders 15 and 17.

Thus, when the apparatus is turned on to function, only one of the visual targets 1 can provide a character, for example any number from "0" to "10", to be seen by a person who use the apparatus. If the person hits a key on the keyboard 3 that would be the same as shown on the target 1 at that time, pulse "1" will go from an output of a comparison circuit 16 to complimentary inputs "F" of flip-flops 11, 12. Shown numbers will be locked up in accordance with information coming from counters 10, 13. In this way both a new number and a clearance to glow the character on the next target 1 will be formed. In other words a new number will be shown on a new target 1. Because of the high frequency in circuit both the number and the target 1 will be of a random choice. If the person hits the wrong key on the keyboard 3, the number shown would stay until the right key is hit.

Counter 18 counts the amount of right hits made by the person and turns off the apparatus when a predetermined amount is achieved. Determination of this amount and also of intervals between sessions depends on the person's age, activities, and visual acuity condition. The amount is set in a set unit 19. The same unit 19 is also used to set the time intervals between consecutive showing characters and their amount within a session. For signalling the person to start a session a timer (see FIG. 3) 20 is provided.

To use the apparatus the person should just unfold the cable 7 to about a straight line on approximately horizontal surface such as a floor, or the surface pieces such as tables, chairs, chests, desks, and so forth. The only requirement to the apparatus arrangement is that each screen of all visual targets 1 could be seen by the person located as close as 0.6' from the first target 1 when the person is in front of it.

The apparatus is preset in accordance with a doctor's recommendations, or a chart provided together with the apparatus, or, later on, the person is experience of using it. According to the preset the timer 20 signals to start a session. Now the person is scanning screens of the visual targets 1 to see a character appeared and then to hit the relevant key on the keyboard 3. The lenses 5 should be in a position when a character on each target 1 could be seen and read by a particular person at a level of minimal discernable size. In other words, the lenses 5 should be put to the right position during the very first session and then adjusted by the person as his or her visual acuity is getting better.

Amount of right hits is also preset for the condition of each particular person. If a hit is wrong the character will stay on a screen until the right hit is made. The better the person's responds the sooner the session is over. This fact forces the person to make every hit right like in a game to sooner reach a result. In order to do it the person should concentrate on every displayed character to read it right. Concentration on the characters located on different distances in the range of 0.5'–20' means training the ciliary muscle within the whole range of its ability to accommodate, and training the portion of the brain where this information is processing. Thus, full general visual acuity therapy is provided. When the predetermined amount of right hits is achieved the apparatus is turned off automatically.

From the description above, one can see that the apparatus is very simple and inexpensive, and the method of using it are very easy to implement in any place without any medical supervision. In the method the human eye ability to accommodate to different subjects of natural human environment within 0.5–20' range is used. This ability can be or is impaired by long periods of eye lens immobility when reading, watching TV, and so on. Tangible results with the therapy in relatively short sessions of eye lens mobility by the method according to the present invention are achieved by enhancing concentration on visual targets within the whole range of natural eye accommodation.

It has to be understood that the general idea of the invention herein described, and the implementation could be modified in different ways. For example, visual targets could have screen of another type, displayed characters size could be adjusted electronically, remote control system could be utilized to control visual targets, different electronic circuit could be used, and so forth.

What I claim is:

1. An acuity therapy apparatus to improve the non-refractive acuity of a person's eyes comprising:

several visual targets;

a control unit;

a keyboard; wherein each of said visual targets having means to display characters and means to adjust apparent size of the displayed characters, said control unit having means for randomly selecting one of said visual targets at a time to display a character and means for randomly generating the character, said keyboard having character means for the person to respond to the character displayed on said one visual target, said control unit having means for comparing said displayed character to responded character and for further commutation depending on the response.

2. The apparatus according to claim 1, wherein means electrically connected with said control unit are provided for presetting an amount of right responses and for counting the right responses and turning off said apparatus when the preset amount is achieved.

3. The apparatus according to claim 1, wherein a timer is provided for signalling the person to start sessions of acuity therapy.

4. The apparatus according to claim 1, wherein said visual targets are equally spaced being connected to a cable having overall length of about 20'.

5. A method for use the apparatus in person's acuity therapy sessions, said method comprising:

a step of placing in front of the person's eyes several visual targets located first at about 0.5' from the person, last at about 20', and the rest equally spaced in between the first and the last a step of causing one of said visual targets at a time in a random order to display one of a number of predetermined characters randomly chosen;

a step of the person to denote through a keyboard a character that the person believes he or she discerns upon said visual target wherein the result of denoting through the keyboard is based on the right responses in comparing the denoted characters and the displayed characters; and a step of the person to repeat denoting through the keyboard until the right response is obtained.

6. The method according to claim 5, further including a step of adjusting the apparent size of said displayed characters upon each of said visual targets to maintain the characters displayed at a level of minimal discernable size.

7. The method according to claim 5, further including a step of setting the amount of characters would be chosen right by the person during one therapy session.

8. The method according to claim 5, further including a step of setting time intervals between said therapy sessions.

* * * * *